US012781199B2

(12) United States Patent
Matsubara

(10) Patent No.: US 12,781,199 B2
(45) Date of Patent: Nov. 3, 2026

(54) MICROORGANISM WITH IMPROVED PROTEIN PRODUCTIVITY AND USE THEREOF

(71) Applicant: AMANO ENZYME INC., Nagoya (JP)

(72) Inventor: Hirotaka Matsubara, Kakamigahara (JP)

(73) Assignee: AMANO ENZYME INC., Nagoya (JP)

( * ) Notice: Subject to any disclaimer, the term of this patent is extended or adjusted under 35 U.S.C. 154(b) by 285 days.

(21) Appl. No.: 18/685,949

(22) PCT Filed: Aug. 30, 2022

(86) PCT No.: PCT/JP2022/032509

§ 371 (c)(1),
(2) Date: Feb. 23, 2024

(87) PCT Pub. No.: WO2023/032950

PCT Pub. Date: Mar. 9, 2023

(65) Prior Publication Data

US 2025/0179422 A1 Jun. 5, 2025

(30) Foreign Application Priority Data

Aug. 30, 2021 (JP) ................................ 2021-139579

(51) Int. Cl.

| | |
|---|---|
| ***C12N 9/00*** | (2006.01) |
| ***C12N 1/20*** | (2006.01) |
| ***C12N 9/28*** | (2006.01) |
| ***C12N 9/80*** | (2006.01) |
| ***C12N 15/90*** | (2006.01) |
| *C12R 1/07* | (2006.01) |

(52) U.S. Cl.

CPC ................. *C12N 9/00* (2013.01); *C12N 1/20* (2013.01); *C12N 9/2417* (2013.01); *C12N 9/80* (2013.01); *C12N 15/902* (2013.01); *C12R 2001/07* (2021.05); *C12Y 302/01001* (2013.01); *C12Y 305/01044* (2013.01)

(58) Field of Classification Search

CPC ....................................................... C12N 9/00

See application file for complete search history.

(56) References Cited

FOREIGN PATENT DOCUMENTS

| | | |
|---|---|---|
| JP | 2012-518388 A | 8/2012 |
| WO | 2010/094064 A1 | 8/2010 |
| WO | 2020/198830 A1 | 10/2020 |

OTHER PUBLICATIONS

WP_013351865.1. NCBI Database. Oct. 25, 2019 (Year: 2019).*

I2C3N5_BACAY. UniProtKB/TrEMBL. Aug. 12, 2020 (Year: 2020).*

Extended European Search Report dated Nov. 20, 2025, issued in the corresponding European patent application No. 22864532.1.

Jari Vehmaanpera et al., "Genetic manipulation of Bacillus amyloliquefaciens," Journal of Biotechnology, 19, 1991, pp. 221-240. (cited in the Nov. 20, 2025 Search Report issued for EP22864532.1).

International Search Report and Written Opinion mailed Oct. 25, 2022, issued for PCT/JP2022/032509.

International Preliminary Report on Patentability dated Mar. 5, 2024, issued for PCT/JP2022/032509 and English translation thereof.

Podlesek, Zdravko et al., "Bacillus licheniformis bacitracin-resistance ABC transporter: relationship to mammalian multidrug resistance," Molecular Microbiology, 1995, 16(5), pp. 969-976.

Multispecies: ABC transporter ATP-binding protein [Bacillus subtilis group] [online], Oct. 2, 2020, [retrieved Oct. 6, 2022], 1 page.

Office Action dated May 12, 2026 issued in corresponding Japanese Patent Application No. 2023-545583, with its English Machine Translation.

Martin Benda et al., "Influence of the ABC Transporter YtrBCDEF of *Bacillus subtilis*on Competence, Biofilm Formation and Cell Wall Thickness," Frontiers in Microbiology, vol. 12, pp. 1-13, 2021.

* cited by examiner

*Primary Examiner* — Yong D Pak

(74) *Attorney, Agent, or Firm* — Troutman Pepper Locke LLP

(57) ABSTRACT

It is an object of the present invention to provide a microorganism with improved protein secretion, and to provide a method for producing a protein using the aforementioned microorganism. According to the present invention, there is provided a microorganism, in which the expression of at least one ABC transporter ATP-binding protein is lost or decreased.

7 Claims, 3 Drawing Sheets

Specification includes a Sequence Listing.

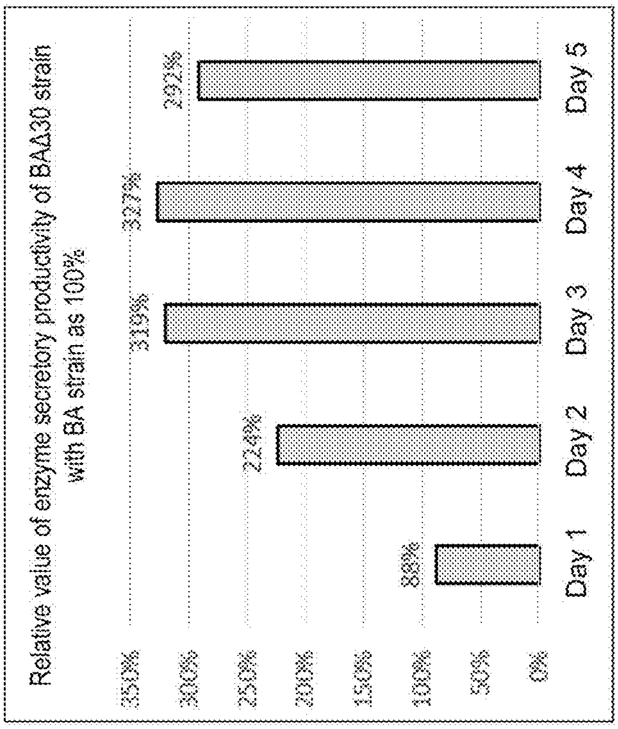
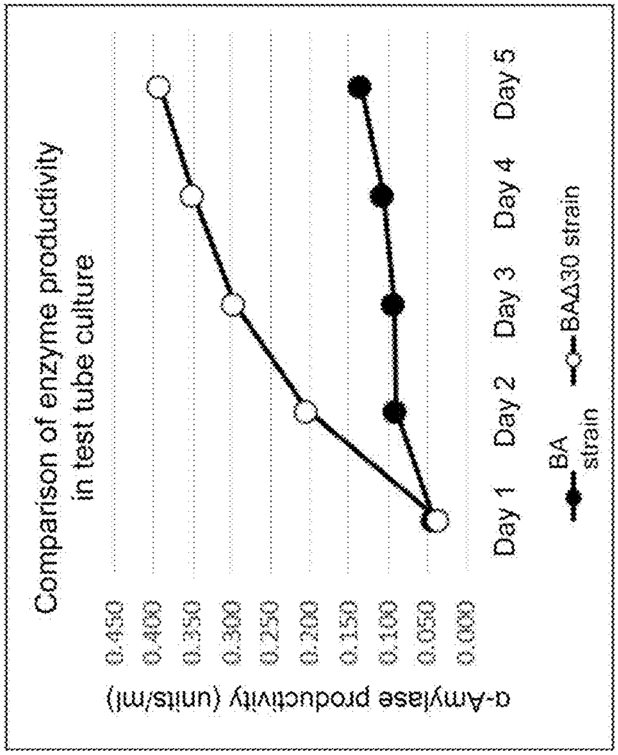
[Fig. 1]

[Fig. 2]
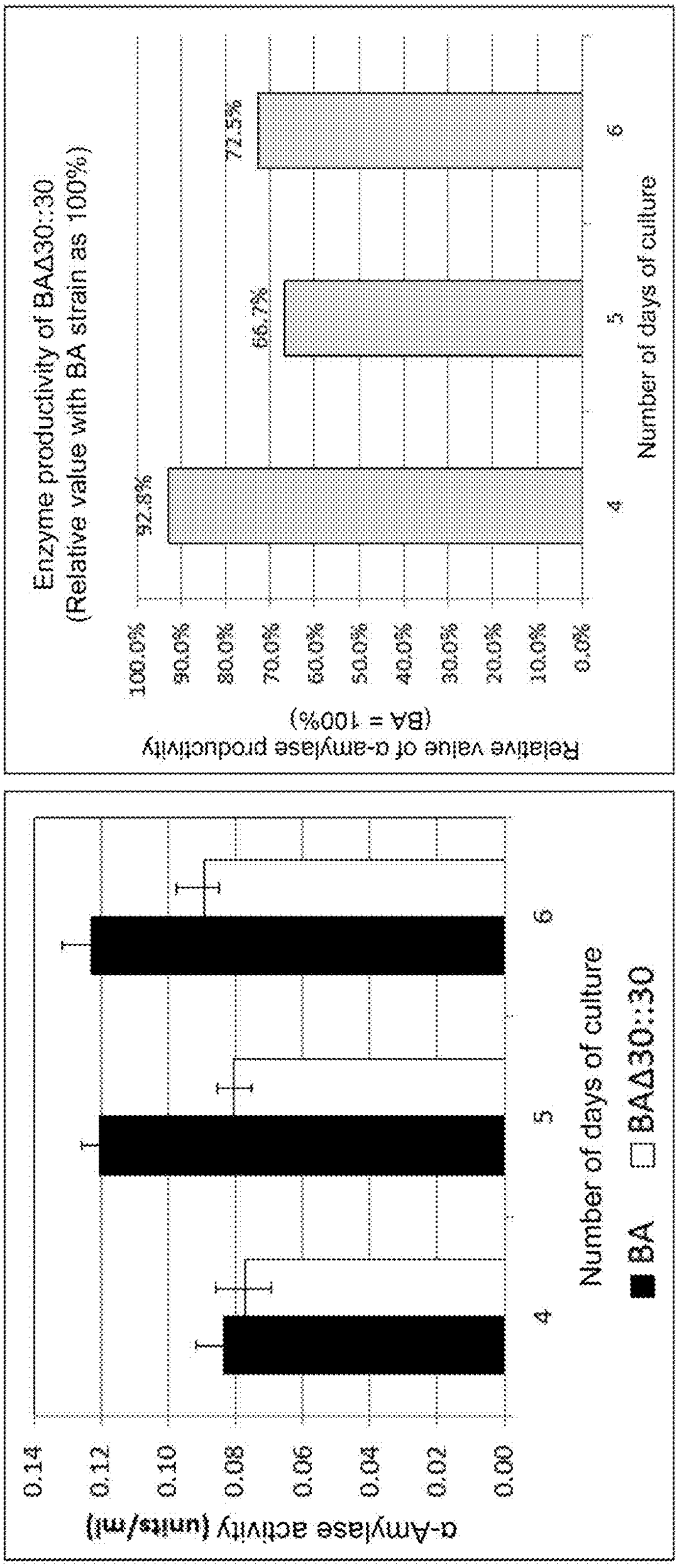

[Fig. 3]
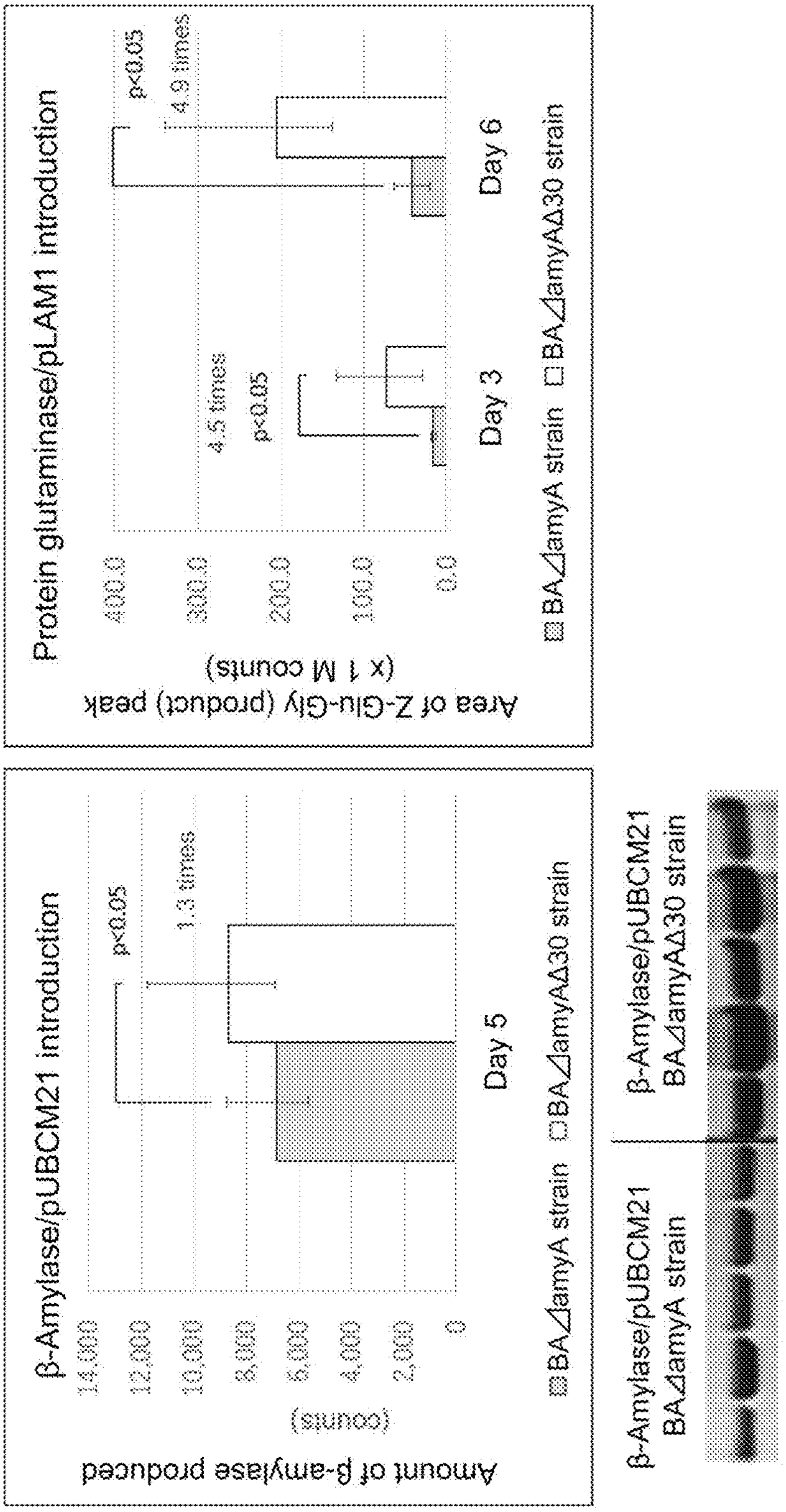

MICROORGANISM WITH IMPROVED PROTEIN PRODUCTIVITY AND USE THEREOF

TECHNICAL FIELD

The present invention relates to a microorganism with improved protein productivity. The present invention further relates to a method for producing a protein using the above-described microorganism.

BACKGROUND ART

Microorganisms of *Bacillus* sp. or the like are advantageous in terms of possible mass secretory production of enzymes, possible ultra-high density culture, rapid growth, many microorganisms belonging to Bio Safety Level 1, Gram-positive bacteria, and relatively small genome size (about 4 M bp). Therefore, microorganisms of *Bacillus* sp. or the like have excellent performance in the production of substances that are utilized in food products and pharmaceutical products. Microorganisms of *Bacillus* sp. or the like are utilized in the production of enzymes such as α-amylase, β-amylase, neutral protease, alkaline protease, and cellulase. In addition, in order to improve the substance-producing ability of microorganisms, acquisition of mutant strains by UV irradiation and acquisition of transformants by genetic recombination technology has been studied.

ATP Binding Cassette (ABC) transporter is a transmembrane protein having a region with an ATP hydrolytic enzyme activity showing a highly common amino acid sequence. The ABC transporter can actively transport compounds by utilizing the energy obtained by hydrolyzing ATP by itself.

Patent Document 1 describes that the ABC transporter is involved in the extracellular export of cyclic peptides produced by the filamentous fungi of *Curvularia* sp. (paragraph 0142). Patent Document 2 describes a method of measuring the amount of the substrate of the ABC protein, and also describes that porphyrins are preferable as such substrates. Patent Document 3 describes an efficient method for producing taurine, and also describes that the activity of the taurine uptake system is decreased by deletion of the tauABC protein gene.

PRIOR ART DOCUMENTS

Patent Documents

Patent Document 1: International Publication WO2018/128140

Patent Document 2: JP Patent Publication No. 2007-151493 A

Patent Document 3: JP Patent Publication No. 2019-129708 A

SUMMARY OF INVENTION

Objects to be Solved by the Invention

As described above, proteins have been produced using microorganisms. However, there is still a need to develop a method of increasing the expression of a protein. The ABC transporter is a gene associated with secretion of small molecules and peptides, but it has not been known that the ABC transporter improves protein secretion.

It is an object of the present invention to provide a microorganism with improved protein secretion. It is another object of the present invention to provide a method for producing a protein using the above-described microorganism.

Means for Solving the Objects

The present inventors have found that enzyme productivity is improved by disrupting an ABC transporter ATP-binding protein gene in a high enzyme-producing strain of *Bacillus amyloliquefaciens*. The present invention has been completed based on the above-described findings.

According to the present invention, the following inventions are provided.

<1> A microorganism, in which the expression of at least one ABC transporter ATP-binding protein is lost or decreased.

<2> The microorganism according to <1>, in which the ABC transporter ATP-binding protein is a protein having an amino acid sequence having a sequence identity of 90% or more to the amino acid sequence as set forth in SEQ ID NO: 2.

<3> The microorganism according to <1> or <2>, which is a *Bacillus* sp. microorganism, a *Cytobacillus* sp. microorganism, or a *Paenibacillus* sp. microorganism.

<4> The microorganism according to any one of <1> to <3>, which is *Bacillus amyloliquefaciens.*

<5> The microorganism according to any one of <1> to <4>, in which the expression of a protein of interest is increased by loss or decrease of the expression of at least one ABC transporter ATP-binding protein.

<6> The microorganism according to <5>, in which the protein of interest is a protein encoded by an endogenous gene or a protein encoded by a foreign gene.

<7> The microorganism according to <5> or <6>, in which the protein of interest is an enzyme.

<8> The microorganism according to any one of <1> to <7>, in which the gene encoding the ABC transporter ATP-binding protein is disrupted by homologous recombination.

<9> A method for producing a protein, including:
culturing the microorganism according to any one of <1> to <8> to produce a protein; and
recovering the obtained protein.

Advantageous Effects of Invention

According to the microorganism of the present invention, secretion of a protein can be improved.

BRIEF DESCRIPTION OF DRAWINGS

FIG. 1 shows the results obtained by confirming the enzyme productivity of a gene-disrupted strain.

FIG. 2 shows the results obtained by confirming the disappearance of an enzyme productivity-enhancing effect by gene complementation.

FIG. 3 shows the results obtained by confirming the enzyme productivity-enhancing effect of a gene-disrupted strain on a heterologous enzyme.

EMBODIMENT OF CARRYING OUT THE INVENTION

In the microorganism of the present invention, the expression of at least one ABC transporter ATP-binding protein is lost or decreased. Preferably, in a microorganism whose genome information, etc. clearly indicates the presence of a gene encoding a protein analogous to the ABC transporter ATP-binding protein shown in the amino acid sequence as set forth in SEQ ID NO: 2, the expression of at least one ABC transporter ATP-binding protein is lost or decreased.

Preferred examples of the microorganism may include a *Bacillus* sp. microorganism, a *Paenibacillus* sp. microorganism, and a *Cytobacillus* sp. microorganism, and the microorganism is more preferably a *Bacillus* sp. microorganism.

Examples of the *Bacillus* sp. microorganism may include *Bacillus amyloliquefaciens, Bacillus siamensis, Bacillus subtilis, Bacillus velezensis, Bacillus nakamurai*, and *Bacillus aquiflavi. More preferred examples of the Bacillus* sp. microorganism may include *Bacillus amyloliquefaciens, Bacillus siamensis, Bacillus subtilis*, and *Bacillus* velezensis. The *Bacillus* sp. microorganism is particularly preferably *Bacillus amyloliquefaciens.*

An example of the *Paenibacillus* sp. microorganism may be *Paenibacillus* sp.

An example of the *Cytobacillus* sp. microorganism may be *Cytobacillus firmus.*

The ABC transporter ATP-binding protein is a protein having an amino acid sequence having a sequence identity of preferably 70% or more, more preferably 75% or more, 80% or more, 85% or more, 90% or more, 93% or more, 95% or more, 97% or more, or 99% or more, to the amino acid sequence as set forth in SEQ ID NO: 2. The ABC transporter ATP-binding protein may be a protein having a structure equivalent to the structure of the present protein, regardless of its functions, and thus, the ABC transporter ATP-binding protein includes annotated proteins, other than the ABC transporter ATP-binding protein. The ABC transporter ATP-binding protein is preferably a protein having an ATP-binding ability.

Preferably, a protein having an amino acid sequence having a sequence identity of 70% or more to the amino acid sequence as set forth in SEQ ID NO: 2 is obtained by the occurrence of conservative amino acid substitution with respect to the amino acid sequence as set forth in SEQ ID NO: 2. The term "conservative amino acid substitution" is used herein to mean that a certain amino acid residue is substituted with an amino acid residue having a side chain with similar properties. Amino acid residues are classified into several families, depending on the side chain thereof; namely, basic side chains (for example, lysine, arginine, and histidine), acidic side chains (for example, aspartic acid and glutamic acid), uncharged polar side chains (for example, glycine, asparagine, glutamine, serine, threonine, tyrosine, and cysteine), non-polar side chains (for example, alanine, valine, leucine, isoleucine, proline, phenylalanine, methionine, and tryptophan), β-branched side chains (for example, threonine, valine, and isoleucine), aromatic side chains (for example, tyrosine, phenylalanine, tryptophan, and histidine), etc. The conservative amino acid substitution is preferably a substitution occurring between amino acid residues in an identical family.

The identity (%) of two amino acid sequences can be determined, for example, by the following procedures. First, two sequences are aligned such that an optimal comparison can be made (for example, a gap may be introduced into a first sequence, so that the alignment with a second sequence may be optimized). When a molecule (amino acid residue) in a specific position of the first sequence is identical to a molecule in a corresponding position in the second sequence, it can be said that the molecules at the positions are identical to each other. The identity of the two sequences is a function of the number of identical positions common in the two sequences (i.e. identity (%)=the number of identical positions/total number of positions×100), and preferably, the number and size of gaps used for optimization of the alignment are also taken into consideration.

Comparison of two sequences and determination of identity can be realized using mathematical algorithms. A specific example of the mathematical algorithm that can be utilized in comparison of sequences may be an algorithm that is described in Karlin and Altschul (1990) Proc. Natl. Acad. Sci. USA 87: 2264-68 and is modified in Karlin and Altschul (1993) Proc. Natl. Acad. Sci. USA 90: 5873-77, but the example of the mathematical algorithm is not limited thereto. The identity of amino acid sequences can be obtained, for example, by blastp (protein-protein BLAST) of National Center for Biotechnology Information (NCBI). As parameters, default parameters may be used. For example, using BLOSUM62 matrix, Gap Costs may be set to be Existence: 11 and Extension: 1.

In the microorganism of the present invention, the expression of at least one ABC transporter ATP-binding protein is lost or decreased.

Loss or decrease in the expression means that the activity of the ABC transporter ATP-binding protein per cell is lost or decreased, compared with a non-modified strain, and includes a case where the activity is completely disappeared. The non-modified strain means a control strain that has not been modified so that the expression of the ABC transporter ATP-binding protein is lost or decreased. The term "loss or decrease in the expression of a protein" specifically means that the number of molecules of the protein per cell is decreased, and/or that the function of the protein per molecule is decreased, compared with the non-modified strain. A decrease in the number of molecules of the protein per cell includes a case where the protein is not present at all. In addition, a decrease in the function of the protein per molecule includes a case where the function of the protein per molecule is completely disappeared. The activity of the protein is not particularly limited, as long as it is decreased, compared with a non-modified strain. For example, the activity of the protein may be decreased to 50% or less, 20% or less, 10% or less, 5% or less, or 0%, compared with a non-modified strain.

A decrease in the expression of a protein means that the expression level of the protein per cell is decreased, compared with that of a non-modified strain such as a wild-type strain or a parental strain. The phrase "the expression of a gene is decreased" specifically means that the transcription amount of a gene (the amount of mRNA) is decreased, and/or that the translation amount of a gene (the amount of a protein) is decreased. The "decrease in the expression of a gene" includes a case where the gene is not expressed at all. It is to be noted that the phrase "the expression of a gene is decreased" is also referred to as "the expression of a gene is weakened." The expression of a gene may be decreased to, for example, 50% or less, 20% or less, 10% or less, 5% or less, or 0%, compared with that of a non-modified strain.

A decrease in the expression of a protein may be due to, for example, a decrease in the transcription efficiency, or a decrease in the translation efficiency, or a combination thereof. A decrease in the expression of a protein can be achieved, for example, by modifying the expression regulatory sequences of a gene, such as a promoter, a Shine-Dargano (SD) sequence (also called a ribosome binding site (RBS)), and a spacer region between RBS and a start codon. In the case of modifying the expression regulatory sequence, the expression regulatory sequence is preferably modified by preferably 1 base or more, more preferably 2 bases or more, and particularly preferably 3 bases or more. In addition, a part or the entire expression regulating sequence may be deleted.

A decrease in the expression of a protein can also be achieved, for example, by manipulating factors involved in regulation of the expression. Examples of the factors involved in regulation of the expression may include small molecules (inductive substances, inhibitory substances, etc.), proteins (transcription factors, etc.), and nucleic acids (siRNA, etc.), which are involved in regulation of the transcription or the translation.

A decrease in the expression of a protein can also be achieved, for example, by introducing a mutation for decreasing the expression of a gene into the coding region of the gene. For example, the expression of a gene can be decreased by replacing a codon in the coding region of a gene with a synonymous codon that is utilized at a lower frequency in a host. In addition, for example, gene expression itself can be decreased by disruption of the gene as described below.

Modification of a protein such that the activity of the protein is decreased can be achieved, for example, by disrupting a gene encoding the protein. The phrase "a gene is disrupted" means that a gene is modified so that it does not produce a normally functioning protein. The phrase "the gene does not produce a normally functioning protein" may include a case where a protein is not produced at all from the gene, and a case where a protein with decreased or disappeared functions per molecule (i.e. activities or properties) is produced from the gene.

Disruption of a gene can be achieved, for example, by deleting a part or the entire coding region of a gene on the chromosome. That is to say, according to the present invention, there is provided a method for producing a microorganism with improved protein productivity, which comprises disrupting a gene encoding at least one ABC transporter ATP-binding protein in a microorganism. In the disruption of a gene, a gene as a whole, including sequences before and after the gene on the chromosome, may be deleted. The region to be deleted may be any one of an N-terminal region, an internal region, a C-terminal region, and the like, as long as a decrease in the activity of a protein can be achieved. In general, the longer the region to be deleted is, the more certainly the gene can be inactivated. Moreover, the sequences before and after the region to be deleted preferably do not match with each other in terms of a reading frame.

Gene disruption can also be achieved, for example, by introducing an amino acid substitution into the coding region of a gene on the chromosome (i.e. missense mutation), or by introducing a stop codon (i.e. nonsense mutation), or by introducing a frameshift mutation involving addition or deletion of 1 or 2 bases.

Gene disruption can also be achieved, for example, by inserting another sequence into the coding region of a gene on the chromosome. The insertion site may be any region of the gene, and the longer the sequence to be inserted is, the more certainly the gene can be inactivated. The sequences before and after the insertion site preferably do not match with each other in terms of a reading frame. Such another sequence is not particularly limited, as long as it decreases or eliminates the activity of an encoded protein. Examples of such another sequence may include marker genes such as antibiotic resistant genes, and genes useful for the production of a substance of interest.

The above-described modification of a gene on the chromosome can be achieved, for example, by creating a deletion-type gene that has been modified not to produce a normally functioning protein, transforming a host with recombinant DNA containing the deletion-type gene, and causing homologous recombination between the deletion-type gene and a wild-type gene on the chromosome, so that the wild-type gene on the chromosome is substituted with the deletion-type gene. At that time, the recombinant DNA may comprise a marker gene, according to the traits of the host, such as nutritional requirements. Examples of the deletion-type genes may include a gene with a deletion of the entire or partial region of the gene, a gene with a missense mutation introduced, a gene with a nonsense mutation introduced, a gene with a frameshift mutation introduced, and a gene with insertion sequences introduced, such as a transposon or a marker gene. The protein encoded by the deletion-type gene, even if it is produced, has a three-dimensional structure that is different from that of a wild-type protein, and their functions are decreased or disappeared. The above-described method of gene disruption by gene replacement utilizing homologous recombination is well known to those skilled in the art.

A decrease in the activity of a protein can be confirmed by measuring the activity of the protein. A decrease in the activity of a protein can also be confirmed by confirming a decrease in the expression of a gene encoding the protein. A decrease in the expression of a gene can be confirmed by confirming a decrease in the transcription amount of the gene, or by confirming a decrease in the amount of a protein expressed from the gene.

A decrease in the transcription amount of a gene can be confirmed by comparing the amount of mRNA transcribed from the gene with that from a non-modified strain. Examples of the method of evaluating the amount of mRNA may include Northern hybridization and RT-PCR. The amount of mRNA may be decreased to, for example, 50% or less, 20% or less, 10% or less, 5% or less, or 0%, compared with that of a non-modified strain.

A decrease in the amount of a protein can be confirmed by performing Western blotting using an antibody. The amount of a protein may be decreased to, for example, 50% or less, 20% or less, 10% or less, 5% or less, or 0%, compared with that of a non-modified strain.

Gene disruption can be confirmed by determining a part or the entire nucleotide sequence of the gene, restriction enzyme map, full-length, or the like, depending on the means used in the disruption.

In the microorganism of the present invention, the expression of a protein of interest is increased by loss or decrease in the expression of at least one ABC transporter ATP-binding protein.

The protein of interest may be either a protein encoded by an endogenous gene, or a protein encoded by a foreign gene.

The protein of interest is not particularly limited, and a protein secreted by secretory signals or a protein that can be secreted by giving secretory signals is exemplified. Specific examples of the protein of interest may include an enzyme, a hormone, an antibody, a growth factor, and a receptor. Among those as described above, the protein of interest is preferably an enzyme. Examples of the enzyme may include various types of industrial enzymes used in food products, detergents, fibers, feeds, chemical products, medicines, diagnostics, etc. Examples of the enzyme may include amylase (α-amylase, β-amylase, etc.), protein glutaminase, protease, xylanase, lipase, laccase, phenol oxidase, oxidase, cutinase, cellulase, hemicellulose, esterase, peroxidase, catalase, glucose oxidase, phytase, pectinase, glucosidase, isomerase, transferase, galactosidase, carbohydrase, phosphatase, and kinase, but are not particularly limited thereto. The enzyme is preferably amylase (α-amylase, β-amylase, etc.), or protein glutaminase.

Examples of the hormone may include, but are not particularly limited to, a follicle-stimulating hormone, a luteinizing hormone, an adrenocorticotropin-releasing factor, somatostatin, a gonadotropin hormone, vasopressin, oxytocin, erythropoietin, and insulin. Examples of the antibody may include, but are not particularly limited to, immunoglobulins. Examples of the growth factor may include, but are not particularly limited to, a platelet-derived growth factor, an insulin-like growth factor, an epidermal growth factor, a nerve growth factor, a fibroblast growth factor, a transforming growth factor, interleukin (e.g., IL-1 to IL-13), interferon, and a colony-stimulating factor.

When the protein of interest is a protein encoded by a foreign gene, a recombinant microorganism can be obtained by incorporating a recombinant vector prepared by binding a DNA fragment encoding the protein of interest with a suitable vector (a plasmid vector, etc.) into a microorganism serving as a host according to a common transformation method. The recombinant vector may comprise a promoter, a signal sequence, a terminator, etc. In addition, as a DNA fragment encoding the protein of interest, a DNA fragment binding to a suitable homologous region with a microorganism genome as a host is used, and this DNA fragment is directly incorporated into the microorganism genome, so that a recombinant microorganism can also be obtained.

<2> Method for Producing Protein

According to the present invention, provided is a method for producing a protein, including a step of culturing the microorganism of the present invention to produce a protein, and a step of recovering the obtained protein.

The culture method and the culture conditions, which are applied in the step of culturing microorganisms to produce proteins, are not particularly limited, as long as the protein of interest is produced. That is, the method and the culture conditions that are suitable for culturing the microorganisms can be determined, as appropriate, on the condition that the protein of interest is produced.

The culture method may be either a liquid culture or a solid culture. The liquid culture is preferable.

The medium is not particularly limited, as long as it is a medium in which microorganisms can grow. Examples of the medium that can be used herein may include those to which the following substances are added: carbon sources, such as glucose, maltose, sucrose, gentiobiose, soluble starch, glycerin, dextrin, molasses, and organic acid; nitrogen sources, such as ammonium sulfate, ammonium carbonate, ammonium phosphate, ammonium acetate, or peptone, yeast extract, corn steep liquor, gelatin, casein hydrolysate, bran, and meat extract; and further, inorganic salts, such as potassium salts, magnesium salts, sodium salts, phosphates, manganese salts, iron salts and zinc salts. In order to promote the growth of microorganisms, vitamins, amino acids and the like may be added to the medium. The pH of the medium is, for example, about 3 to 10, and preferably about 7 to 8. The culture temperature is usually about 10° C. to 50° C., preferably about 20° C. to 37° C., and the microorganisms are cultured for 1 to 7 days under aerobic conditions. Examples of the culture method may include a shaking culture method, and an aerobic deep culture method using a jar fermenter.

After completion of the culture, a protein of interest is recovered from the culture solution or the culture mass. When the protein is recovered from the culture solution, for example, the culture supernatant is filtered, centrifuged, etc. to remove insoluble matters, and thereafter, the resultant is separated and purified by appropriately combining concentration using an ultrafiltration membrane, salting-out such as ammonium sulfate precipitation, dialysis, and various types of chromatography using ion exchange resin, etc., thereby obtaining the protein of interest.

On the other hand, when a protein of interest is recovered from the cell mass, for example, the cell mass is crushed by a pressure treatment, an ultrasonic treatment, etc., and the resultant is then separated and purified in the same manner as that described above, so as to obtain the present enzyme. Besides, the cell mass may be previously recovered from the culture solution by filtration, a centrifugation treatment, etc., and thereafter, the above-described series of steps (crushing, separation, and purification of the cell mass) may be carried out.

As a method of measuring the expression of a protein of interest in microorganisms, an immunological analysis method using a polyclonal or monoclonal antibody specific to the protein can be used. Examples of the immunological analysis method may include enzyme-linked immunoassay (ELISA), radioimmunoassay (RIA), fluorescence immunoassay (FIA), and fluorescence-activated cell sorting (FACS), but are not particularly limited thereto. Otherwise, the expression of a protein of interest can also be measured by measuring the activity of the protein of interest in microorganisms.

EXAMPLES

<Composition of Pre-Culture Medium>

| | |
|---|---|
| Polypeptone | 3.0 w/v % |
| Yeast extract | 1.0 w/v % |
| D-glucose | 0.1 w/v % |

<Composition of Main Culture Medium>

| | |
|---|---|
| Maltose | 5.00 w/v % |
| Yeast extract | 2.00 w/v % |
| Fish gelatin | 1.00 w/v % |
| Sodium chloride | 1.00 w/v % |
| Fish meat extract | 0.30 w/v % |
| Sodium dihydrogen phosphate dodecahydrate | 0.13 w/v % |
| Manganese chloride tetrahydrate | 0.02 w/v % |
| Antifoaming agent | Moderate amount |

<Method of Evaluating α-Amylase Productivity>

Since α-amylase is expressed in a large amount, the amount of enzyme secreted and produced was determined by appropriately diluting the α-amylase, and then measuring the activity of the enzyme. The α-amylase assay kit manufactured by Kikkoman Biochemifa Company was employed, and 1.5 ml of a liquid as a standard protocol was downscaled to 240 μl, while maintaining the ratio, and was then used to the measurement of the activity.

<Method of Evaluating β-Amylase Productivity>

Since the expression level of β-amylase was significant, the band on SDS-PAGE was quantified by densitometry analysis, and was then used for comparison.

<Method of Evaluating Protein Glutaminase Productivity>

Since the expression level of protein glutaminase is low, a comparison was made in terms of the amount of the enzyme secreted and produced, using the area of the reaction product obtained as a result of the measurement according to a HPLC method. The method of measuring the activity of protein glutaminase according to the HPLC method is described below.

| PG activity measurement method (HPLC method) | |
|---|---|
| Synthetic substrate solution for measurement of PG activity | 5 mM |
| Z-Gln-Gly (PEPTIDE INSTITUTE, INC.) | |
| 5% TritonX-100 sol. | 0.0023% (v/v) |
| 0.2M Monopotassium disodium phosphate (pH 6.5) | Dissolved in 3 ml |
| Hippuric acid solution (internal specimen) | 6.5 mM |
| Hippuric acid | |
| 0.2M Monopotassium disodium phosphate (pH6.5) | Dissolved in 10 ml |

Reaction

A sample solution (10 μl) was mixed with a substrate solution (130 μl), and the obtained mixture was then reacted at 37° C. for any given time. After completion of the reaction, 10 d of a hippuric acid solution as an internal specimen was added to the reaction mixture, followed by mixing, and the obtained mixture was subjected to MF filtration and then to HPLC. Detection was carried out according to HPLC, using the following column under the following run conditions.

| Column: ZORBAX SB-C18 (2.1 × 50 mm), 1.8 μm | |
|---|---|
| Solvent A: | 0.1% TFA/$H_2O$ |
| Solvent B: | 0.1% TFA/acetonitrile |
| Program: | 0-0.3 min B: 10% |
| | 0.3-2.0 min_B: 10%-25% |
| | 2.0-2.2 min_B: 25% |
| | 2.2-3.0 min_B: 100% |
| Injection volume: | 2 μL |
| Flow rate: | 1.0 mL/min |
| Detection: | UV 205 nm |

Example 1: Confirmation of Enzyme Productivity of Gene-Disrupted Strain (Strains Used)

BA Strain

The BA strain is a strain having a high ability to produce α-amylase, which was obtained by bleeding a *Bacillus amyloliquefaciens* (NBRC 15535) strain used as a parent strain. The BA strain and the *Bacillus amyloliquefaciens* (NBRC 15535) strain have almost the same genes, and have an identical ABC transporter ATP-binding protein gene. Thus, it is assumed that almost the same effects will be obtained even in the case of using *Bacillus amyloliquefaciens* (NBRC 15535).

BAΔ30 Strain

The BAΔ30 strain is a strain obtained by disrupting a No. 30 gene on the genome of the BA strain according to homologous recombination. The above-described No. 30 gene is a gene encoding the ABC transporter ATP-binding protein. The nucleotide sequence of the No. 30 gene is shown in SEQ ID NO: 1 in the sequence listing, and the amino acid sequence encoded by the No. 30 gene is shown in SEQ ID NO: 2 in the sequence listing.

```
                                      (SEQ ID NO: 1)
atgcacgcgattgagctgaagcaattaactaaacattataaagaaaccg

ccgctgttgaccgacttgaattttcaattgaaaaaggagaatttttcgc

tttactcggagagaacggagccggaaaaacgacattaatccggatgctt

tgcggcctcctttctccagatgaaggtgatgcatcagtgcttggtcaca
```

-continued

```
gcattttgactgatttggataaaataaaaccgaaaatgaatatgtctcc

gcaggaaacagccatcgcccctaatttaaccgtacgggaaaacttagag

tttatagccggagtctacggaattccgaaaaaagaaggaaaaaaaagaa

cggatgagatgctcgaattgtttcaattaaaagaaaaagaaagagaaaa

aacaaaaacgttatcaggcggaatgcagcgccggctcagcatcgcaatg

ggaatgattacaaaaccggatatttatttcttagatgagccgacattag

gtctggacgtccgttcacgccgcgagttgtggaaaaatcttgagtcatt

aaagggagacatgacgatcattttaacgacacactatctagaagaagct

gaagccctggcagaccgtatttgcattttagaaaatgggacattaaaag

cactgggtacggctgaggacctgaaaaagcaaactcattcagccacatt

tgaagatgccttttttagcgatttgtgacggggaggcggggctttatgct

tga

                                      (SEQ ID NO: 2)
MHAIELKQLTKHYKETAAVDRLEFSIEKGEFFALLGENGAGKTTLIRML

CGLLSPDEGDASVLGHSILTDLDKIKPKMNMSPQETAIAPNLTVRENLE

FIAGVYGIPKKEGKKRTDEMLELFQLKEKEREKTKTLSGGMQRRLSIAM

GMITKPDIYFLDEPTLGLDVRSRRELWKNLESLKGDMTIILTTHYLEEA

EALADRICILENGTLKALGTAEDLKKQTHSATFEDAFLAICDGEAGLYA
```

The BA strain was transformed by introducing DNA for homologous recombination into it, and selection was then carried out based on Kanamycin resistance, so that primary recombinants were selected by culture at 42° C. Subsequently, secondary selection was carried out based on Kanamycin sensitivity, and homologous recombination was then confirmed by colony PCR. Protoplast purification (monocellular isolation) was performed, and a BAΔ30 strain was obtained as a gene-disrupted strain.

(Culture Method)

Each strain was inoculated into a test tube containing 5 ml of a preculture medium, and a reciprocating shaking culture was then carried out at 37° C. for 18 hours. The preculture solution was inoculated in an amount of 2% (v/v) into a test tube containing 5 ml of a main culture medium, and a reciprocating shaking culture was then carried out at 37° C. From the first day of the culture, sampling was carried out every 24 hours until the fifth day of the culture, and the amount of α-amylase produced in the culture supernatant was measured by activity measurement, and the amount of the enzyme secreted and produced was confirmed.

The results are shown in FIG. 1. The α-amylase productivity of the BA strain was increased by about 3 times by disruption of the No. 30 gene.

Example 2: Confirmation of Disappearance of Enzyme Productivity-Enhancing Effect by Gene Complementation In order to confirm whether the enzyme productivity-enhancing effect of the BAΔ30 strain is certainly caused by disruption of the No. 30 gene, the No. 30 gene on the genome of the BAΔ30 strain was repaired to the original one by homologous recombination. With regard to confirmation of the complementary strain BAΔ30::30 of the No. 30 gene obtained by homologous recombination, it was confirmed by whole genome sequencing that the complementation is certainly held without deviation. Regarding the BAΔ30::30 strain that is the complementary strain of the No. 30 gene on the genome, the enzyme production-enhancing effect of the BAΔ30::30 strain was confirmed by the same method as that of Example 1.

The results are shown in FIG. 2. The enzyme productivity-enhancing effect disappeared by complementation of the No. 30 gene.

Example 3: Confirmation of Enzyme Productivity-Enhancing Effect of Gene-Disrupted Strain on Heterologous Enzyme It could be confirmed that the secretory productivity of endogenous α-amylase is improved by disruption of the No. 30 gene. In order to confirm whether this effect caused by disruption of the No. 30 gene is limited to secretory production of α-amylase, the following experiment was carried out.

<3-1> Confirmation of *Bacillus flexus*-Derived β-Amylase Productivity-Enhancing Effect Using a BAΔamyA strain involving disruption of an α-amylase gene on the genome of the BA strain for the recombinant expression of a heterologous enzyme, the disrupted strain BAΔamyAΔ30 was constructed by homologous recombination of the No. 30 gene.

pUBCM21 is an *E. coli/Bacillus subtilis* shuttle vector, in which a pUC plasmid commonly used in *E. coli* was allowed to bind to a pUB plasmid commonly used in *Bacillus subtilis*. The foreign gene, *Bacillus flexus*-derived β-amylase, was incorporated into an expression vector (pUBCM21) with a chimeric expression cassette produced by combining an endogenous α-amylase-derived promoter, a *Bacillus circulans*-derived pullulanase-derived signal sequence, and a terminator, so as to produce a β-amylase/pUBCM21 vector. The produced β-amylase/pUBCM21 vector was introduced into each of the BAΔamyA strain and the BAΔamyAΔ30 strain according to a protoplast-PEG method. After completion of the culture performed by the same method as that of Example 1, the expression level of β-amylase was confirmed by SDS-PAGE to determine the amount of the enzyme secreted and produced.

<3-2> Confirmation of *Chryseobacterium proteolyticum*-Derived Protein Glutaminase Productivity-Enhancing Effect pLAM1 is a pUB plasmid. A *Chryseobacterium proteolyticum*-derived protein glutaminase mature sequence was incorporated into an expression vector (pLAM1) with an amyA-type expression cassette consisting of an α-amylase-derived promoter, a signal sequence and a terminator, each of which is endogenous, so as to produce a protein glutaminase/pLAM1 vector. The produced protein glutaminase/pLAM1 vector was introduced into each of the BAΔamyA strain and the BAΔamyAΔ30 strain according to a protoplast-PEG method. After completion of the culture performed by the same method as that of Example 1, the amount of the enzyme secreted and produced was confirmed from protein glutaminase activity.

The results are shown in FIG. 3.

The secretory expression levels of both of the foreign enzyme genes β-amylase and protein glutaminase were increased by the A30 strain. It was revealed that the enzyme productivity-enhancing effect caused by disruption of the No. 30 gene is also exhibited upon the expression of heterologous enzymes.

INDUSTRIAL APPLICABILITY

According to the microorganism of the present invention, secretion of a useful protein such as an enzyme can be improved. The present invention is useful for production of a useful protein such as an enzyme.

The present invention is not limited to the above-described embodiments and examples of the invention in any way. The present invention includes various modifications that can be easily conceived of by a person skilled in the art without departing from the scope of claims. The contents of the study papers, published patent publications, patent publications, and the like that are explicitly specified in the present description shall be cited by incorporating the entire contents thereof.

SEQUENCE LISTING

```
Sequence total quantity: 2
SEQ ID NO: 1            moltype = DNA  length = 738
FEATURE                 Location/Qualifiers
source                  1..738
                        mol_type = genomic DNA
                        organism = Bacillus amyloliquefaciens
CDS                     1..738
SEQUENCE: 1
atgcacgcga ttgagctgaa gcaattaact aaacattata aagaaaccgc cgctgttgac  60
cgacttgaat tttcaattga aaaaggagaa tttttcgctt tactcggaga gaacggagcc  120
ggaaaaacga cattaatccg gatgctttgc ggcctccttt ctccagatga aggtgatgca  180
tcagtgcttg gtcacagcat tttgactgat ttggataaaa taaaaccgaa aatgaatatg  240
tctccgcagg aaacagccat cgcccctaat ttaaccgtac gggaaaactt agagtttata  300
gccggagtct acggaattcc gaaaaaagaa ggaaaaaaaa gaacggatga gatgctcgaa  360
ttgtttcaat taaaagaaaa agaaagagaa aaaacaaaaa cgttatcagg cggaatgcag  420
cgccggctca gcatcgcaat gggaatgatt acaaaaccgg atatttattt cttagatgag  480
ccgacattag gtctggacgt ccgttcacgc cgcgagttgt ggaaaaatct tgagtcatta  540
aagggagaca tgacgatcat tttaacgaca cactatctag aagaagctga agccctggca  600
gaccgtattt gcattttaga aaatgggaca ttaaaagcac tggtacggc tgaggacctg  660
aaaaagcaaa ctcattcagc cacatttgaa gatgcctttt tagcgatttg tgacggggag  720
```

-continued

```
gcggggcttt atgcttga                                         738

SEQ ID NO: 2          moltype = AA  length = 245
FEATURE               Location/Qualifiers
source                1..245
                      mol_type = protein
                      organism = Bacillus amyloliquefaciens
SEQUENCE: 2
MHAIELKQLT KHYKETAAVD RLEFSIEKGE FFALLGENGA GKTTLIRMLC GLLSPDEGDA  60
SVLGHSILTD LDKIKPKMNM SPQETAIAPN LTVRENLEFI AGVYGIPKKE GKKRTDEMLE  120
LFQLKEKERE KTKTLSGGMQ RRLSIAMGMI TKPDIYFLDE PTLGLDVRSR RELWKNLESL  180
KGDMTIILTT HYLEEAEALA DRICILENGT LKALGTAEDL KKQTHSATFE DAFLAICDGE  240
AGLYA                                                       245
```

The invention claimed is:

1. A microorganism, wherein the expression of at least one ABC transporter ATP-binding protein is lost or decreased, wherein the ABC transporter ATP-binding protein is a protein having an amino acid sequence having a sequence identity of 90% or more to the amino acid sequence as set forth in SEQ ID NO: 2, wherein the expression of a protein of interest is increased by loss or decrease of the expression of at least one ABC transporter ATP-binding protein.

2. The microorganism according to claim 1, which is a *Bacillus* sp. microorganism, a *Cytobacillus* sp. microorganism, or a *Paenibacillus* sp. microorganism.

3. The microorganism according to claim 1, which is *Bacillus amyloliquefaciens.*

4. The microorganism according to claim 1, wherein the protein of interest is a protein encoded by an endogenous gene or a protein encoded by a foreign gene.

5. The microorganism according to claim 1, wherein the protein of interest is an enzyme.

6. The microorganism according to claim 1, wherein the gene encoding the ABC transporter ATP-binding protein is disrupted by homologous recombination.

7. A method for producing a protein, comprising:

culturing the microorganism according to claim 1 to produce a protein; and recovering the obtained protein.

* * * * *